United States Patent [19]
Finkenzeller et al.

[11] Patent Number: 4,521,899
[45] Date of Patent: Jun. 4, 1985

[54] DENTAL X-RAY DIAGNOSTIC DEVICE

[75] Inventors: Johann Finkenzeller; Wolfgang Mittelstaedt, both of Erlangen, Fed. Rep. of Germany

[73] Assignee: Siemens Aktiengesellschaft, Berlin & Munich, Fed. Rep. of Germany

[21] Appl. No.: 442,898

[22] Filed: Nov. 19, 1982

[30] Foreign Application Priority Data

Dec. 15, 1981 [DE] Fed. Rep. of Germany ....... 3149723

[51] Int. Cl.³ .............................................. A61B 6/14
[52] U.S. Cl. ..................................................... 378/40
[58] Field of Search .............................. 378/38, 39, 40

[56] References Cited
U.S. PATENT DOCUMENTS 4,419,764 12/1983 Kinanen ................................ 378/40

Primary Examiner—Alfred E. Smith
Assistant Examiner—T. N. Grigsby
Attorney, Agent, or Firm—Hill, Van Santen, Steadman & Simpson

[57] ABSTRACT

A dental X-ray diagnostic device for producing panoramic layer exposures of a subject particularly panoramic layer exposures of a jaw characterized by an X-ray source mounted on an arm of a carriage, a cassette which receives X-ray film and is rotatably mounted on the arm so that when the arm of the carriage is rotated both the source and cassette rotate around the subject with the cassette also being rotated relatively on the arm and a slit diaphragm having a changeable effective width for varying the thickness of the layer in which sharp images can be obtained.

8 Claims, 2 Drawing Figures

DENTAL X-RAY DIAGNOSTIC DEVICE

BACKGROUND OF THE INVENTION

The present invention is directed to a dental X-ray diagnostic device for producing panoramic layer exposures of the subject particularly of a jaw. The device comprises an X-ray source which is mounted on a rotating arm of a carriage, a cassette which accepts the X-ray film and is mounted to rotate on the arm so that the film is moved during an exposure as the arm rotates both the source and cassette around the subject and a slit diaphragm disposed in the beam path between the source and the subject for limiting the width of the beam of radiation projected from the source.

A dental X-ray diagnostic device for producing panoramic layer exposures of a subject such as a jaw of a patient are known and have been sold. An example is disclosed in a Siemens brochure entitled ORTHOPAN-TOMOGRAPH No. MD 80/1238. As disclosed in this brochure, the diagnostic device provides a panoramic layer exposure or a panograph of a jaw as the patient's skull is fixed in a special support mount and the device has a mechanism which rotates the X-ray tube and the cassette containing the film around the patient so that the entire jaw can be imaged on the film with a single exposure. The image gained with this device is a layered image which is only sharp for the subject at a very specific layer depth while the zones adjacent the specific depth are blurred. The thickness of the sharply imaged zone is thereby proportional to the radius of curvature of the layer form and inversely proportional to the slit width of the X-ray beam. In the known devices which have a constant slit width over the entire motion sequence, the so-called normal layer, which comprises the jaw area including the front teeth, has a different layer thickness because of the different curvatures of the patient's jaw.

In order to achieve an appropriate radiation intensity for the entire area to be imaged without those areas for which such an intensity is not required being overloaded radiation-wise, it is known from German OS No. 2,753,119 to design a diaphragm which is positioned between the radiation source and the subject to be exposed with a wedge-shaped slit which converges downward. With the assistance of such a wedge-shaped slit diaphragm, the intensity of the radiation is greater in the upper area of the jaw than in the lower area. Thus, differing layer thicknesses of the subject in the vertical plane can be taken into consideration but the X-ray beam remains constant as viewed over the entire exposure of the jaw.

Due to the tighter curvature of the jaw in the area of the front teeth, a lower layer thickness is present there. This provides disadvantages particularly given subjects whose jaws depart from the normal shape. For example, if the dentitions with teeth are extremely slanted or with projecting canine, the images of these slanted teeth or projecting canines will not always have sufficient sharpness.

SUMMARY OF THE INVENTION

The present invention is directed to the object of achieving an improvement in the construction of a diagnostic device which will have the goal of attaining a layer thickness which is optimally matched to the subject over the entire exposure. To accomplish these goals, the present invention is directed to an improvement in a dental X-ray diagnostic device for producing panoramic layer exposures of the subject, particularly panoramic layer exposures of a jaw, said device comprising an X-ray source, carriage means having an arm for supporting the X-ray source, a cassette-accepting X-ray film, said cassette being mounted for relative movement on the arm of the carriage means, said carriage means moving both the X-ray source and the cassette around the subject with the cassette being moved relatively on the arm and a slit diaphragm means being positioned between the source and the subject for limiting the width of the beam of radiation being projected from the source. The improvement comprises adjustment means for changing the effective width of the slit diaphragm means during an exposure.

The present invention is directed to the perception that taking into consideration that the sharply imaged zone of an exposure principally depends on the radius of curvature of the subject to be exposed and on the width of the beam of X-rays. It is proposed for achieving the desired object to make the effective slit width of the diaphragm which is disposed between the radiation source and the cassette variable during the exposure. This diaphragm variation in terms of its effective slit width can be provided in place of the already existing primary or secondary diaphragm or can be provided as an additional diaphragm. It is particularly advantageous to couple this to the primary diaphragm so that the patient thereby receives the lowest radiation dose and to accomplish the coupling by use of a cam plate. This can be adjustably mounted for translational movement. A particularly simple execution of the variable diaphragm being mounted for rotation are on a vertical axis and by so doing the edges limiting the slit thus form the effective slit width which limits the width of the X-ray beam.

DESCRIPTION OF THE PREFERRED EMBODIMENTS

The principles of the present invention are particularly useful when incorporated in a dental X-ray diagnostic device for producing panoramic layer exposures of a patient's jaw. The basic structure of such a device is known as mentioned by the above cited brochure.

Figure 1:
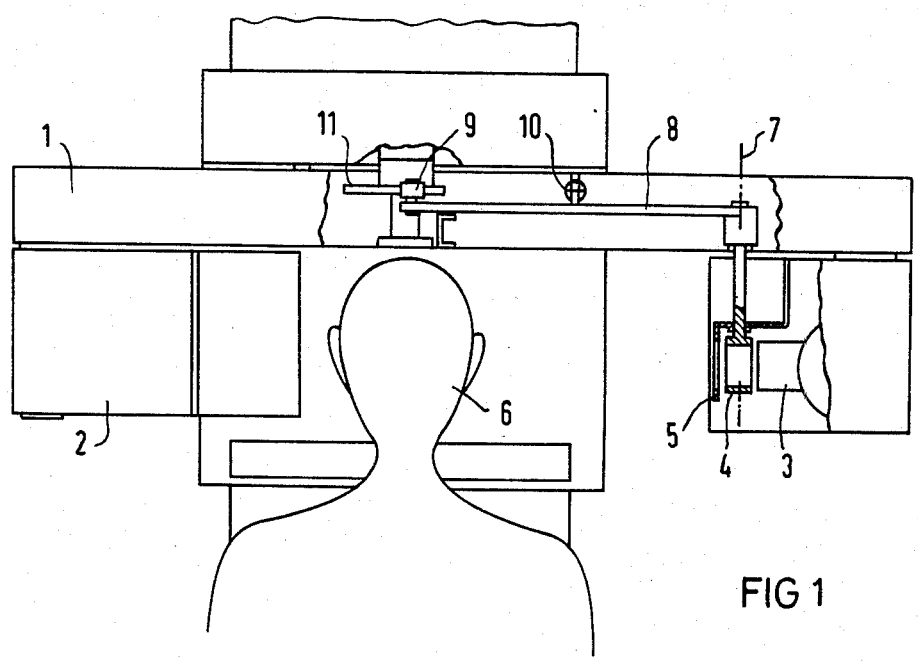
FIG. 1 is a side view of a dental X-ray diagnostic means for producing a panoramic layer in accordance with the present invention with portions in section.
Figure 2:
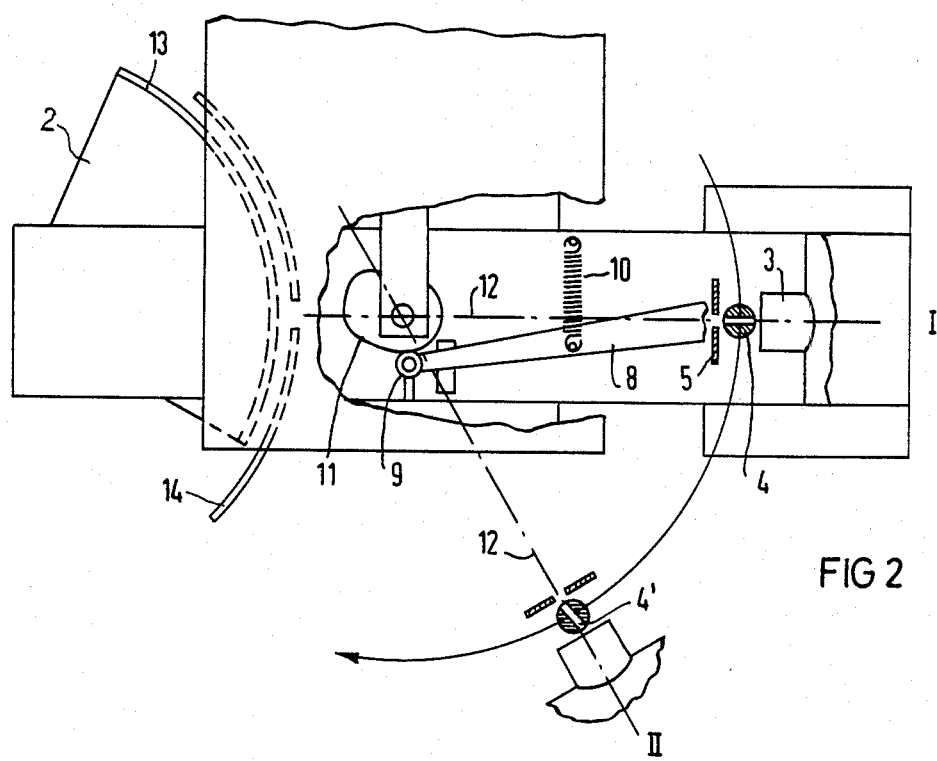
FIG. 2 is a plan view of the device according to FIG. 1 with portions in section and illustrating two different positions of the source.

The device essentially consists of an arm 1 of a carriage which is mounted for height adjustment on a support. The arm 1 carries a cassette 2 which accepts an X-ray film which is illustrated in FIG. 2 as being in a curved path 13. As illustrated, the cassette 2 is mounted for rotation about an axis on the arm 1. On the opposite end of the arm 1 an X-ray source 3 having two diaphragms 4 and 5 is provided. The diaphragm 4 is a slit diaphragm and is variable in terms of its effective slit width while the diaphragm 5 is a standard primary diaphragm. The arm 1 with the film cassette 2 and the X-ray source 3 having the two diaphragms 4 and 5 will be rotated in a known manner around the patient's head 6 during an exposure. During the rotation, the effective gating of the X-ray beam proceeding from the radiation source 3 is varied by means of twisting or rotating the diaphragm 4. To accomplish this, the diaphragm 4 is mounted by mounting means in the arm 1 to rotate around a vertical bearing axis 7. In addition, the diaphragm is connected to a lever 8 which on the other end has a cam follower 9 which is held on a radial cam 11 by a spring 10. In comparison to the rotating arm 1, the radial cam 11 is stationarily disposed and the cam has a shape which determines the angular position of the diaphragm 4 with reference to the cental beam focus 10 which is indicated by the line 12.

As illustrated in FIG. 2, the diaphragm 4 is shown in two different positions. In the position indicated by I, the full slit width of the diaphragm is utilized. In the position indicated by II, the diaphragm has been rotated so that its effective width 4' is smaller. Thus, due to the rotation of the diaphragm on the axis 7 between the position illustrated at I and the position II, the effective slit width has become narrower. Due to this constriction of the slit width, the thickness of the layer in which a sharp image will be obtained is increased so that object points which according to the previous method would lie outside of the layer thickness and would be blurred now or sharply imaged.

The cam plate 11 is designed in such a manner that the effective slit width becomes narrower when exposing the area of the front teeth. Thus, the layer thickness for obtaining sharp images is increased in this area. In the area of the temporomaxillary joints, however, the full slit width is given and thus the normal layer thickness will be achieved.

In FIG. 2, a secondary diaphragm 14 is disposed directly in front of the position 13 for the film. The secondary diaphragm advantageously correspondingly proportionally couples to the variable diaphragm 4 so that an optimum limitation of the ray beam is given while avoiding scattered rays.

It has proved to be particularly advantageous to compensate the radiation intensity over the entire cycle range in accordance with the varying slit width of the diaphragm 4. For example, it is desirable to increase the intensity when the slit width becomes smaller. By so doing, over-exposures or, respectively, under-exposures, can be avoided.

Although various minor modifications may be suggested by those versed in the art, it should be understood that we wish to embody within the scope of the patent granted hereon, all such modifications as reasonably and properly come within the scope of our contribution to the art.

We claim:

1. In a dental X-ray diagnostic device for producing panoramic layer exposures of a subject particularly panoramic layer exposures of a jaw, said device comprising an X-ray source, carriage means having an arm for supporting the X-ray source, a cassette accepting X-ray film, said cassette being mounted for relative movement on the arm of the carriage means, said carriage means moving both the X-ray source and cassette around a subject with the cassette being moved relatively on the arm and a slit diaphragm means comprising a slit diaphragm being positioned between the source and the subject for limiting the width of a beam of radiation being projected from the source, the improvement comprising means for changing the layer thickness to match the subject during the entire exposure including adjustment means for changing the effective width of the slit diaphragm during an exposure, said adjustment means including means for mounting the slit diaphragm for rotation on a vertical axis to change the effective width of the slit and a cam plate coupled to said slit diaphragm to control the rotation thereof, said cam plate being designed in such a manner that the slit diaphragm is rotated to a position to constrict the effective slit width of the diaphragm to achieve a greater layer thickness while exposing the area of the front teeth.

2. In a dental X-ray diagnostic device according to claim 1, which includes a primary diaphragm positioned adjacent said slit diaphragm and between said X-ray source and the subject.

3. In a dental X-ray diagnostic device according to claim 1, wherein said adjustment means includes a lever attached to said slit diaphragm, said lever having a follower riding on a cam surface of the cam plate so as the source and cassette rotate about the subject, said diaphragm is rotated to provide the desired layer thickness for the area being exposed.

4. In a dental X-ray diagnostic device according to claim 1, which includes a secondary diaphragm being disposed between the subject and the cassette to block scattered rays from said film.

5. In a dental X-ray diagnostic device for producing panoramic layer exposures of a subject particularly panoramic layer exposures of a jaw, said device comprising an X-ray source, carriage means having an arm for supporting the X-ray source, a cassette accepting X-ray film, said cassette being mounted for relative movement on the arm of the carriage means, said carriage means moving both the X-ray source and cassette around a subject with the cassette being moved relatively on the arm, a slit diaphragm means being positioned between the source and the subject for limiting the width of a beam of radiation being projected from the source, and a secondary diaphragm being disposed between the subject and the cassette to block scattered rays from said film, the improvements comprising means for changing the layer thickness to match the subject during the entire exposure including adjustment means for changing the effective width of said slit diaphragm means during the exposure, said adjustment means including a cam plate for controlling the effective width of said slit diaphragm means, said cam plate being designed in such a manner that it constricts the effective slit width of the slit diaphragm means in order to achieve a greater layer thickness while exposing the area of the front teeth of the subject.

6. In a dental X-ray diagnostic device according to claim 5, which includes a primary diaphragm positioned adjacent said slit diaphragm means and between said X-ray source and subject.

7. In a dental X-ray diagnostic device according to claim 5, wherein the slit diaphragm means comprises a slit diaphragm, said adjustment means includes means for mounting said slit diaphragm for rotation on a vertical axis and a lever attached to said slit diaphragm and having a follower engaging a cam surface of the cam plate so that as the carriage rotates the slit diaphragm is rotated about a vertical axis in response to movement of the follower along the cam surface of the cam plate.

8. In a dental X-ray diagnostic device according to claim 7, which includes a primary diaphragm positioned adjacent said slit diaphragm and between said X-ray source and the subject.

* * * * *